United States Patent [19]

Maurer et al.

[11] 4,136,176
[45] Jan. 23, 1979

[54] O-ALKYL-O-[6-SUBSTITUTED-THIO-PYRIDAZIN-3-YL]-(THIONO) (THIOL)-PHOSPHORIC (PHOSPHONIC) ACID ESTERS

[75] Inventors: Fritz Maurer; Reiner A. Fuchs, both of Wuppertal; Ingeborg Hammann, Cologne; Wolfgang Behrenz, Overath-Steinenbrueck, all of Germany

[73] Assignee: Bayer Aktiengesellschaft, Leverkusen, Germany

[21] Appl. No.: 800,603

[22] Filed: May 25, 1977

[30] Foreign Application Priority Data

Jun. 16, 1976 [DE] Fed. Rep. of Germany ....... 2627075

[51] Int. Cl.$^2$ .......................... C07D 9/65; A01N 9/36
[52] U.S. Cl. ..................................... 424/200; 544/232
[58] Field of Search ................. 260/250 AP; 424/200; 544/232

[56]  References Cited
U.S. PATENT DOCUMENTS 3,878,210  5/1975  Lorenz ........................... 260/250 AP

FOREIGN PATENT DOCUMENTS 1284320  8/1972  United Kingdom .............. 260/239 AP Primary Examiner—Nicholas S. Rizzo
Assistant Examiner—Mark L. Berch
Attorney, Agent, or Firm—Sprung, Felfe, Horn, Lynch & Kramer

[57]  ABSTRACT

O-alkyl-O-[6-substituted-thio-pyridazin-3-yl]-(thiono) (thiol)-phosphoric (phosphonic) acid esters of the formula

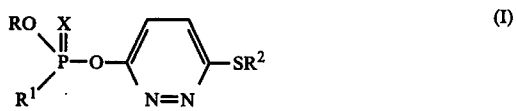

in which
R represents alkyl,
$R^1$ represents alkyl, alkylthio or alkylamino,
$R^2$ represents alkyl, alkenyl, alkynyl or phenyl which can optionally be monosubstituted or polysubstituted, and
X represents oxygen or sulphur.
which possess insecticidal and acaricidal properties.

9 Claims, No Drawings

O-ALKYL-O-[6-SUBSTITUTED-THIO-PYRIDAZIN-3-YL]-(THIONO)(THIOL)-PHOSPHORIC (PHOSPHONIC) ACID ESTERS

The present invention relates to and has for its objects the provision of particular new O-alkyl-O-[6-substituted-thiopyridazin-3-yl]-(thiono) (thiol)-phosphoric (phosphonic) acid esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DOS 1,770,067 that O-pyridazinylthionophosphoric-(phosphonic) acid esters, for example O,O-diethyl-O-[6-oxo-pyridazin(3)yl]-thionophosphoric acid ester (Compound A) and O-ethyl-O-[6-oxo-pyridazin(3)yl]-thionomethane-(Compound B) and -ethane-phosphonic acid ester (Compound C), possess insecticidal and acaricidal properties.

The present invention provides substituted pyridazinyl(thiono)(thiol)-phosphoric(phosphonic) acid ester derivatives of the general formula

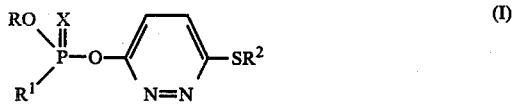

in which
R represents alkyl,
R$^1$ represents alkyl, alkylthio or alkylamino,
R$^2$ represents alkyl, alkenyl, alkynyl or phenyl which can optionally be monosubstituted or polysubstituted, and
X represents oxygen or sulphur.

Preferably, R represents straight-chain or branched alkyl with 1 to 4 carbon atoms, R$^1$ represents straight-chain or branched alkyl with 1 to 3 carbon atmoms or straight-chain or branched alkylthio or monoalkylamino with 1 to 4 carbon atoms per alkyl moiety, R$^2$ represents straight-chain or branched alkyl with 1 to 4 carbon atoms, alkenyl or alkynyl with 2 to 4 carbon atoms, phenyl, or alkylthiophenyl with 1 to 3 carbon atoms in the alkylthio radical, and X represents sulphur.

Surprisingly, the substituted pyridazinyl(thiono)(thiol)-phosphoric(phosphonic) acid ester derivatives according to the invention exhibit a better insecticidal and acaricidal action than the corresponding O-pyridazinylthionophosphoric(phosphonic) acid esters of analogous structure and of the same type of action. The products according to the present invention accordingly represent a genuine enrichment of the art.

The invention also provides a process for the preparation of a substituted pyridazinyl(thiono)(thiol)-phosphoric(phosphonic) acid ester derivative of the formula (I) in which a (thiono)(thiol)-phosphoric(phosphonic) acid ester halide or ester-amide halide of the general formula

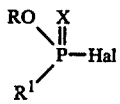

in which
R, R$^1$ and X have the above-mentioned meanings and Hal represents halogen, preferably chlorine, is reacted with a 3-hydroxy-pyridazine of the formula

in which
R$^2$ has the above-mentioned meaning, optionally in the presence of an acid acceptor or in the form of an alkali metal salt, alkaline earth metal salt or ammonium salt, optionally in the presence of a solvent or diluent.

If, for example, O,S-diethylthionothiolphosphoric acid diester chloride and 3-hydroxy-6-propargylthio-pyridazine are used as starting materials, the course of the reaction can be represented by the following formula scheme:

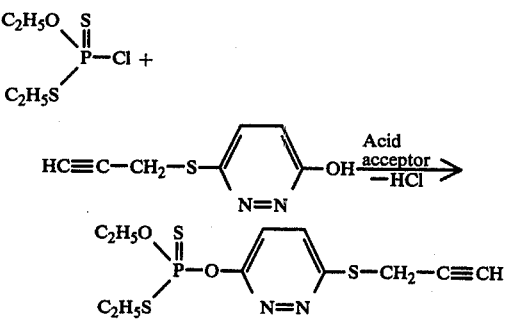

The (thiono)(thiol)-phosphoric(phosphonic) acid ester halides and ester-amide halides (II) are described in the literature and can be prepared in accordance with generally customary processes. The following may be mentioned as individual examples thereof: O,S-dimethyl-, O,S-diethyl-, O,S-di-n-propyl-, O,S-di-iso-propyl-, O,S-di-n-butyl, O,S-di-iso-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-thionothiol-phosphoric acid diester chloride, as well as O-methyl-, O-ethyl-, O-n-propyl-, O-iso-propyl-, O-n-butyl-, O-iso-butyl-, O-sec.-butyl- and O-tert.-butyl-methane-, -ethane-, -n-propane- and -iso-propane-thionophosphonic acid ester chloride, and also O,N-dimethyl-, O,N-diethyl-, O,N-di-n-propyl-, O,N-di-iso-propyl-, O,N-di-n-butyl-, O,N-di-iso-butyl-, O,N-di-sec.-butyl-, O-methyl-N-ethyl-, O-ethyl-N-n-propyl-, O-ethyl-N-iso-propyl-, O-ethyl-N-n-butyl-, O-n-propyl-N-ethyl-, O-n-propyl-N-iso-propyl-, O-n-propyl-N-sec.-butyl-, O-iso-propyl-N-ethyl-, O-iso-propyl-N-n-propyl-, O-iso-propyl-N-n-butyl-, O-n-butyl-N-ethyl-, O-n-butyl-N-n-propyl-, O-n-butyl-N-iso-butyl-, O-sec.-butyl-N-ethyl-, O-sec.-butyl-N-n-propyl- and O-tert.-butyl-N-ethyl-thionophosphoric acid ester-amide chloride.

The 3-hydroxy-pyridazines (III) are known and can be prepared in accordance with generally customary processes. The following may be mentioned as individual examples thereof: 6-methylthio-, 6-ethylthio-, 6-n-propylthio-, 6-isopropylthio-, 6-n-butylthio-, 6-sec.-butylthio-, 6-tert.-butylthio, 6-isobutylthio-, 6-allylthio-, 6-but-2-enylthio-, 6-but-3-enylthio-, 6-phenylthio-, 6-(4-methylthiophenylthio)-, 6-(4-ethylthiophenylthio)-, 6-(4-n-propylthiophenylthio)- and 6-(4-iso-propylthiophenylthio)-3-hydroxy-pyridazine.

The reaction according to the invention is preferably carried out in the presence of a solvent or diluent. Virtually all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 120°, preferably at 20° to 60° C.

In general, the reaction is allowed to take place under normal pressure.

For carrying out the process, the starting materials are preferably employed in the equimolar ratio. An excess of one or other component produces no essential advantages. The reactants are in general combined in one of the abovementioned solvents, if appropriate in the presence of an acid acceptor, and are in most cases stirred for several hours at an elevated temperature to complete the reaction.

Thereafter the batch may be poured into an organic solvent, for example toluene, and the organic phase worked up in the usual manner by washing, drying and distilling off the solvent.

The new compounds are mostly obtained in the form of oils, which in some cases cannot be distilled without decomposition, but can be freed from the last volatile constituents by so-called "slight distillation," that is to say by prolonged heating under reduced pressure to moderately elevated temperatures, and they can be purified in this way. They are characterized by the refractive index. Some compounds are crystalline and possess a sharp melting point.

As already mentioned, the substituted pyridazinyl(thiono)(thiol)-phosphoric(phosphonic) acid ester derivatives according to the invention are distinguished by an excellent insecticidal and acaricidal activity. They are not only active against plant pests but also against hygiene pests and pests of stored products, and combine a low phytotoxicity with a good action against both sucking and biting insects and mites.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating animal pests, especially insects and arachnida which are encountered in agriculture, in forestry, in the protection of stored products and of materials, and in the hygiene field. They are active against normally sensitive and resistant species and against all or some stages of development. The abovementioned pests include:

From the order of the Isopoda, for example *Oniscus asellus, Armadillidium vulgare* and *Porcellio scaber*. From the order of the Diplopoda, for example *Blaniulus guttulatus*. From the order of the Chilopoda, for example *Geophilus carpophagus* and *Scutigera spec.* From the order of the Symphyla, for example *Scutigerella immaculata*. From the order of the Thysanura, for example *Lepisma saccharina*. From the order of the Collembola, for example *Onychiurus armatus*. From the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria*. From the order of the Dermaptera, for example *Forficula auricularia*. From the order of the Isoptera, for example *Reticulitermes* spp.. From the order of the Anoplura, for example *Phylloxera vastatrix, Pemphigus* spp., *Pediculus humanus corporis, Haematopinus* spp. and *Linognathus* spp. From the order of the Mallophaga, for example *Trichodectes* spp. and *Damalinea* spp. From the order of the Thysanoptera, for example *Hercinothrips femoralis* and *Thrips tabaci*. From the order of the Heteroptera, for example *Eurygaster* spp., *Dysdercus intermedius, Piesma quadrata, Cimex lectularius, Rhodnius prolixus* and *Triatoma* spp. From the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.. From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana*. From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus holoeucus, Gibbium psylloides, Tribolium* spp., *Tenebrio molitor, Agriotes* spp., *Conode-* rus spp., *Melolontha melolontha, Amphimallon solstitialis* and *Costelytra zealandica.* From the order of the Hymenoptera, for example *Diprion* spp., *Hoplocampa* spp., *Lasius* spp., *Monomorium pharaonis* and *Vespa* spp. From the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.* From the order of the Siphonaptera, for example *Xenopsylla cheopis* and *Ceratophyllus* spp.. From the order of the Arachnida, for example *Scorpio maurus* and *Latrodectus mactans.* From the order of the Acarina, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., and *Tetranychus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules or inorganic and organic meals, and granules or organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides and acaricides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: — 3 parts by weight of acetone
Emulsifier: — 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 1:

Table 1
(*Plutella* Test)

| Active compound | Active compound concentration in % by weight | Degree of destruction in % after 3 days |
|---|---|---|
| $(C_2H_5O)_2\overset{S}{\overset{\|}{P}}-O-\underset{\underset{H}{N-N}}{\diagup\!\!=\!\!\diagdown}=O$ (known) (A) | 0.1<br>0.01 | 100<br>0 |
| $\underset{iso-C_3H_7O}{\overset{CH_3}{\diagdown}}\overset{S}{\underset{\|}{P}}-O-\underset{N-N}{\diagup\!\!=\!\!\diagdown}-SCH_3$ (2) | 0.1<br>0.01 | 100<br>100 |
| $\underset{iso-C_3H_7O}{\overset{CH_3}{\diagdown}}\overset{S}{\underset{\|}{P}}-O-\underset{N-N}{\diagup\!\!=\!\!\diagdown}-SC_3H_7\text{-iso}$ (14) | 0.1<br>0.01 | 100<br>100 |
| $\underset{C_2H_5}{\overset{CH_3O}{\diagdown}}\overset{S}{\underset{\|}{P}}-O-\underset{N-N}{\diagup\!\!=\!\!\diagdown}-SCH_3$ (1) | 0.1<br>0.01 | 100<br>100 |
| $\underset{C_2H_5}{\overset{CH_3O}{\diagdown}}\overset{S}{\underset{\|}{P}}-O-\underset{N-N}{\diagup\!\!=\!\!\diagdown}-SC_2H_5$ (10) | 0.1<br>0.01 | 100<br>100 |

Table 1-continued
(*Plutella* Test)
| Active compound | Active compound concentration in % by weight | Degree of destruction in % after 3 days |
|---|---|---|
| 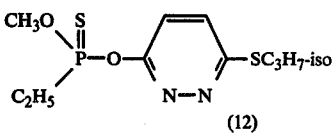 (12) | 0.1<br>0.01 | 100<br>100 |
| 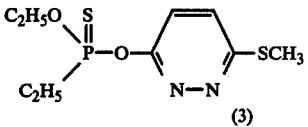 (3) | 0.1<br>0.01 | 100<br>100 |
| 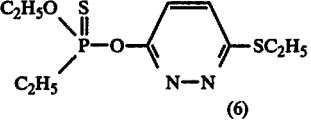 (6) | 0.1<br>0.01 | 100<br>100 |
| 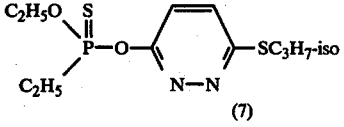 (7) | 0.1<br>0.01 | 100<br>100 |
| 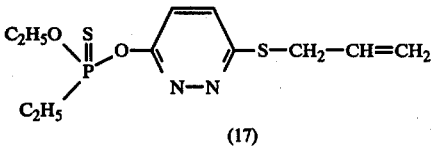 (17) | 0.1<br>0.01 | 100<br>100 |
| 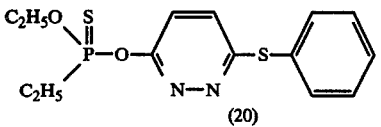 (20) | 0.1<br>0.01 | 100<br>100 |
| 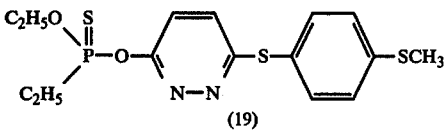 (19) | 0.1<br>0.01 | 100<br>100 |
| 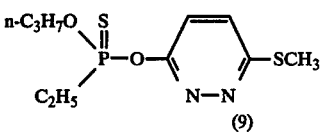 (9) | 0.1<br>0.01 | 100<br>100 |
| 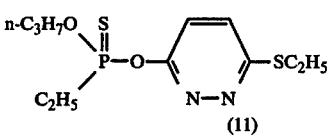 (11) | 0.1<br>0.01 | 100<br>100 |
| 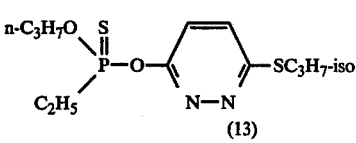 (13) | 0.1<br>0.01 | 100<br>100 |
| 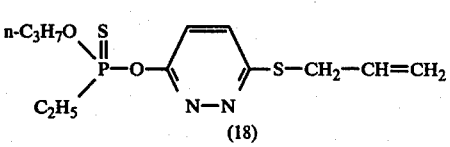 (18) | 0.1<br>0.01 | 100<br>100 |

Table 1-continued

(*Plutella* Test)

| Active compound | Active compound concentration in % by weight | Degree of destruction in % after 3 days |
|---|---|---|
| 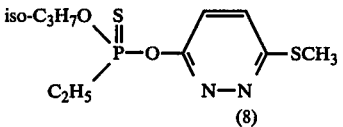 (8) | 0.1<br>0.01 | 100<br>100 |
| 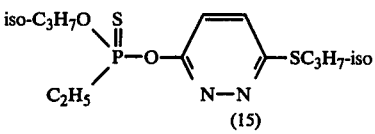 (15) | 0.1<br>0.01 | 100<br>100 |
| 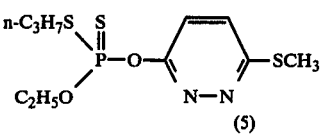 (5) | 0.1<br>0.01 | 100<br>100 |

EXAMPLE 2

Tetranychus test (resistant)
Solvent: — 3 parts by weight of acetone
Emulsifier: — 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the common or two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 2:

Table 2

(*Tetranychus* Test)

| Active compound | Active compound concentration in % by weight | Degree of destruction in % after 2 days |
|---|---|---|
| 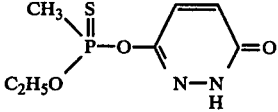 (known) (B) | 0.1<br>0.01 | 95<br>0 |
| 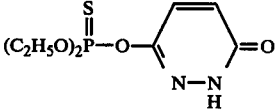 (known) (A) | 0.1<br>0.01 | 95<br>0 |
| 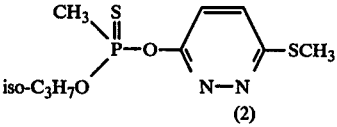 (2) | 0.1<br>0.01 | 99<br>99 |
| 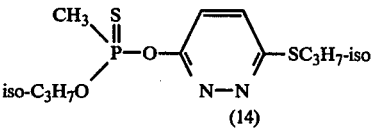 (14) | 0.1<br>0.01 | 100<br>100 |

Table 2-continued
(Tetranychus Test)

| Active compound | Active compound concentration in % by weight | Degree of destruction in % after 2 days |
|---|---|---|
| Compound (1): $(CH_3O)(C_2H_5)P(=S)-O-$[pyridazine]$-SCH_3$ | 0.1 / 0.01 | 98 / 95 |
| Compound (10): $(CH_3O)(C_2H_5)P(=S)-O-$[pyridazine]$-SC_2H_5$ | 0.1 / 0.01 | 100 / 100 |
| Compound (12): $(CH_3O)(C_2H_5)P(=S)-O-$[pyridazine]$-SC_3H_7\text{-iso}$ | 0.1 / 0.01 | 100 / 100 |
| Compound (3): $(C_2H_5O)(C_2H_5)P(=S)-O-$[pyridazine]$-SCH_3$ | 0.1 / 0.01 | 98 / 98 |
| Compound (6): $(C_2H_5O)(C_2H_5)P(=S)-O-$[pyridazine]$-SC_2H_5$ | 0.1 / 0.01 | 100 / 100 |
| Compound (7): $(C_2H_5O)(C_2H_5)P(=S)-O-$[pyridazine]$-SC_3H_7\text{-iso}$ | 0.1 / 0.01 | 100 / 100 |
| Compound (17): $(C_2H_5O)(C_2H_5)P(=S)-O-$[pyridazine]$-S-CH_2-CH=CH_2$ | 0.1 / 0.01 | 100 / 99 |
| Compound (9): $(n\text{-}C_3H_7O)(C_2H_5)P(=S)-O-$[pyridazine]$-SCH_3$ | 0.1 / 0.01 | 100 / 100 |
| Compound (11): $(n\text{-}C_3H_7O)(C_2H_5)P(=S)-O-$[pyridazine]$-SC_2H_5$ | 0.1 / 0.01 | 100 / 100 |
| Compound (13): $(n\text{-}C_3H_7O)(C_2H_5)P(=S)-O-$[pyridazine]$-SC_3H_7\text{-iso}$ | 0.1 / 0.01 | 100 / 100 |
| Compound (18): $(n\text{-}C_3H_7O)(C_2H_5)P(=S)-O-$[pyridazine]$-S-CH_2-CH=CH_2$ | 0.1 / 0.01 | 100 / 100 |

Table 2-continued

(Tetranychus Test)

| Active compound | Active compound concentration in % by weight | Degree of destruction in % after 2 days |
|---|---|---|
| (8) iso-C3H7O, C2H5, P(=S)–O–[pyridazine]–SCH3 | 0.1<br>0.01 | 100<br>90 |
| (15) iso-C3H7O, C2H5, P(=S)–O–[pyridazine]–SC3H7-iso | 0.1<br>0.01 | 100<br>100 |
| (4) C2H5O, iso-C3H7–NH, P(=S)–O–[pyridazine]–SCH3 | 0.1<br>0.01 | 99<br>95 |

EXAMPLE 3

$LT_{100}$ test for Diptera
Test animals: — Aedes aegypti
Solvent: — Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test animals were then placed in the Petri dish and it was covered with a glass lid.

The condition of the test animals was continuously observed. The time which was necessary for 100% destruction was determined.

The test animals, the active compounds, the concentrations of the active compounds and the times at which there was 100% destruction can be seen from the following Table 3:

Table 3

$LT_{100}$ test for Diptera (Aedes aegypti)

| Active compound | Active compound concentration of the solution in % by weight | $LT_{100}$ in minutes (') ltr. hours (hrs) |
|---|---|---|
| (C) (known) C2H5, C2H5O, P(=S)–O–[pyridazine]=O, N–N–H | 0.2<br>0.02 | 180<br>3 h - 0% |
| (1) CH3O, C2H5, P(=S)–O–[pyridazine]–SCH3 | 0.02 | 60 |
| (3) C2H5O, C2H5, P(=S)–O–[pyridazine]–SCH3 | 0.02 | 60 |
| (2) iso-C3H7O, CH3, P(=S)–O–[pyridazine]–SCH3 | 0.02 | 60 |

Table 3-continued

LT$_{100}$ test for Diptera (Aedes aegypti)

| Active compound | Active compound concentration of the solution in % by weight | LT$_{100}$ in minutes (') ltr. hours (hrs) |
|---|---|---|
| (9) n-C$_3$H$_7$O\P(=S)(C$_2$H$_5$)-O-[pyridazinyl]-SCH$_3$ | 0.02 | 180 |
| (10) CH$_3$O\P(=S)(C$_2$H$_5$)-O-[pyridazinyl]-SC$_2$H$_5$ | 0.02 | 180 |
| (6) C$_2$H$_5$O\P(=S)(C$_2$H$_5$)-O-[pyridazinyl]-SC$_2$H$_5$ | 0.02 | 180 |
| (11) n-C$_3$H$_7$O\P(=S)(C$_2$H$_5$)-O-[pyridazinyl]-SC$_2$H$_5$ | 0.02 | 180 |
| (12) CH$_3$O\P(=S)(C$_2$H$_5$)-O-[pyridazinyl]-SC$_3$H$_7$-iso | 0.02 | 180 |
| (7) C$_2$H$_5$O\P(=S)(C$_2$H$_5$)-O-[pyridazinyl]-SC$_3$H$_7$-iso | 0.02 | 180 |
| (14) iso-C$_3$H$_7$O\P(=S)(CH$_3$)-O-[pyridazinyl]-SC$_3$H$_7$-iso | 0.02 | 120 |
| (16) CH$_3$O\P(=S)(C$_2$H$_5$)-O-[pyridazinyl]-S-CH$_2$-CH=CH$_2$ | 0.02 | 180 |
| (17) C$_2$H$_5$O\P(=S)(C$_2$H$_5$)-O-[pyridazinyl]-S-CH$_2$-CH=CH$_2$ | 0.02 | 180 |
| (18) n-C$_3$H$_7$O\P(=S)(C$_2$H$_5$)-O-[pyridazinyl]-S-CH$_2$-CH=CH$_2$ | 0.2 | 60 |
| (20) C$_2$H$_5$O\P(=S)(C$_2$H$_5$)-O-[pyridazinyl]-S-C$_6$H$_5$ | 0.02 | 180 |

Table 3-continued

LT₁₀₀ test for *Diptera (Aedes aegypti)*

| Active compound | Active compound concentration of the solution in % by weight | LT₁₀₀ in minutes (') ltr. hours (hrs) |
|---|---|---|
| 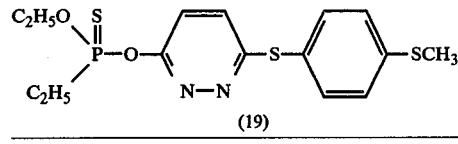 (19) | 0.02 | 180 |

The following examples are set forth to illustrate, without limitation, the manner of producing the instant compounds accroding to the present invention:

EXAMPLE 4

(a) The 3-hydroxypyridazines (III) which were used as starting materials were prepared as follows:

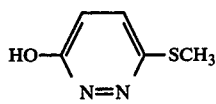

A solution of 96 g (0.6 mol) of 3-chloro-6-methylthiopyridazine and 98.4 g (1.2 mols) of sodium acetate in 500 ml of glacial acetic acid was boiled for 2 hours under reflux. The solvent was then distilled off in vacuo, the residue was triturated with water and the reaction product was filtered off. In this way, 55.8 g (65% of theory) of 3-hydroxy-6-methylthiopyridazine were obtained in the form of a beige powder of melting point 119° C.

The following compounds of the formula

 (III)

were prepared analogously:

Table 4

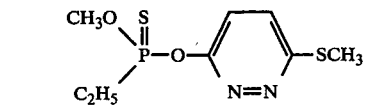

| R² | Yield (% of theory) | Physical data (melting point, ° C; refractive index) |
|---|---|---|
| C₂H₅ | 69 | 83 |
| iso-C₃H₇ | 85 | 108 |
| CH≡C—CH₂— | 38 | 157 |
| CH₂=CH—CH₂— | 67 | 89 |
| CH₃S—⟨⟩— | 90 | 168 |
| ⟨⟩ | 62 | n_D^{27}:1.6655 | b)

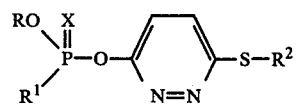 (1)

A mixture of 13 g (0.09 mol) of 3-hydroxy-6-methylthiopyridazine, 18.6 g (0.135 mol) of potassium carbonate, 250 ml of acetonitrile and 14.3 g (0.09 mol) of O-methylethanethionophosphonic acid ester chloride was stirred for 4 hours at 45° C. The reaction mixture was then poured into 400 ml of toluene and washed twice with 300 ml of water at a time. The toluene solution was dried over sodium sulphate and evaporated in vacuo. The residue was triturated with petroleum ether and the product was filtered off after crystallization. In this way, 13.5 g (57% of theory) of O-methyl-O-[6-methylthio-pyridazin-3-yl]-ethanethionophosphonic acid ester were obtained in the form of a beige powder of melting point 58° C.

EXAMPLE 5

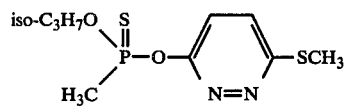 (2)

17.3 g (0.1 mol) of O-iso-propyl-methanethionophosphonic acid ester chloride were added dropwise, at room temperature, to a suspension of 18 g (0.1 mol) of the sodium salt of 3-hydroxy-6-methylthio-pyridazine in 250 ml of acetonitrile. The mixture was then stirred for 6 hours at 45° C., cooled and mixed with 400 ml of toluene. This mixture was extracted by shaking twice with 300 ml of water at a time, the toluene solution was dried over sodium sulphate and the solvent was distilled off in vacuo. The residue was triturated with petroleum ether and after crystallization the product was filtered off. 17 g (61% of theory) of O-iso-propyl-O-[6-methylthiopyridazin-3-yl]-methanethionophosphonic acid ester were thus obtained in the form of a beige powder of melting point 51° C.

The following compounds of the formula $$\begin{array}{c} RO \\ \diagdown \\ R^1 \end{array} \begin{array}{c} X \\ \| \\ P \end{array} - O - \underset{N=N}{\diagup\!\!\!\diagdown} - S - R^2 \quad (L)$$

were prepared analogously:

Table 5

| Compound No. | R | R¹ | R² | X | Yield (% of theory) | Physical data (melting point, °C refractive index) |
|---|---|---|---|---|---|---|
| 3 | $C_2H_5$ | $C_2H_{15}$ | $CH_3$ | S | 44 | 49 |
| 4 | $C_2H_5$ | iso-$C_3H_7$—NH— | $CH_3$ | S | 49 | $n_D^{25}$:1.5498 |
| 5 | $C_2H_5$ | n-$C_3H_7$S | $CH_3$ | S | 53 | $n_D^{25}$:1.5743 |
| 6 | $C_2H_5$ | $C_2H_5$ | $C_2H_5$ | S | 58 | $n_D^{21}$:1.5531 |
| 7 | $C_2H_5$ | $C_2H_5$ | iso-$C_3H_7$ | S | 59 | $n_D^{25}$:1.5520 |
| 8 | iso-$C_3H_7$ | $C_2H_5$ | $CH_3$ | S | 25 | 129 |
| 9 | n-$C_3H_7$ | $C_2H_5$ | $CH_3$ | S | 25 | 105 |
| 10 | $CH_3$ | $C_2H_5$ | $C_2H_5$ | S | 43 | 51 |
| 11 | n-$C_3H_7$ | $C_2H_5$ | $C_2H_5$ | S | 52 | $n_D^{25}$:1.5472 |
| 12 | $CH_3$ | $C_2H_5$ | iso-$C_3H_7$ | S | 31 | 57 |
| 13 | n-$C_3H_7$ | $C_2H_5$ | iso-$C_3H_7$ | S | 56 | $n_D^{25}$:1.5440 |
| 14 | iso-$C_3H_7$ | $CH_3$ | iso-$C_3H_7$ | S | 59 | $n_D^{25}$:1.5465 |
| 15 | iso-$C_3H_7$ | $C_2H_5$ | iso-$C_3H_7$ | S | 20 | 91 |
| 16 | $CH_3$ | $C_2H_5$ | $CH_2=CH-CH_2-$ | S | 43 | $n_D^{23}$:1.5775 |
| 17 | $C_2H_5$ | $C_2H_5$ | $CH_2=CH-CH_2-$ | S | 54 | $n_D^{23}$:1.5594 |
| 18 | n-$C_3H_7$ | $C_2H_5$ | $CH_2=CH-CH_2-$ | S | 48 | $n_D^{23}$:1.5815 |
| 19 | $C_2H_5$ | $C_2H_5$ | 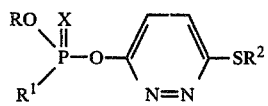 | S | 62 | 74 |
| 20 | $C_2H_5$ | $C_2H_5$ | 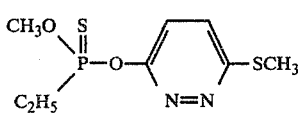 | S | 70 | $n_D^{26}$:1.6040 |

It will be appreciated that the instant specification and examples are set forth by way of illustration and not limitation, and that various modifications and changes may be made without departing from the spirit and scope of the present invention.

What is claimed is:

1. An O-alkyl-O-[6-substituted-thio-pyridazin-3-yl]-(thiono) (thiol)-phosphoric (phosphonic) acid ester of the formula $$\begin{array}{c} RO \\ \diagdown \\ R^1 \end{array} \!\!\! \begin{array}{c} X \\ \| \\ P-O \end{array} \!\!\!-\!\!\! \begin{array}{c} \\ \\ N=N \end{array} \!\!\!-SR^2$$

in which
R is alkyl,
R¹ is alkyl, alkylthio or alkylamino,
R² is alkyl, alkenyl, alkynyl phenyl or alkylthiophenyl, and
X is oxygen or sulphur.

2. An ester according to claim 1, in which
R is alkyl with 1 to 4 carbon atoms,
R¹ is alkyl with 1 to 3 carbon atoms, or alkylthio or monoalkylamino with 1 to 4 carbon atoms per alkyl moiety,
R² is alkyl with 1 to 4 carbon atoms, alkenyl with 2 to 4 carbon atoms, phenyl or mono-alkylthiophenyl with 1 to 3 carbon atoms in the alkylthio radical, and
X is sulphur.

3. An ester according to claim 1, wherein such ester is O-methyl-O-[6-methylthio-pyridazin-3-yl]-ethanethionophosphonic acid ester of the formula

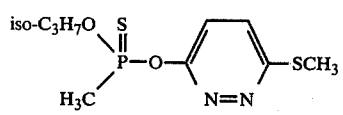

4. An ester according to claim 1, wherein such ester is O-iso-propyl-O-[6-methylthiopyridazin-3-yl]-methanethionophosphonic acid ester of the formula

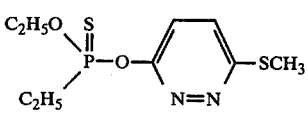

5. An ester according to claim 1, wherein such ester is O-ethyl-O-[6-methylthiopyridazin-3-yl]-ethanethionophosphonic acid ester of the formula

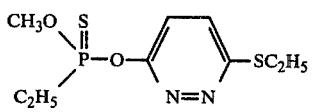

6. An ester according to claim 1, wherein each ester is O-methyl-O-[6-ethylthio-pyridazin-3-yl]-ethanethionophosphonic acid ester of the formula

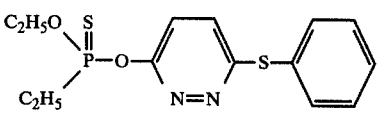

7. An ester according to claim 1, wherein such ester is O-ethyl-O-[6-phenylthio-pyridazin-3-yl]-ethanethionophosphonic acid ester of the formula 8. An insecticidal or acaricidal composition containing as active ingredient an insecticidally or acaricidally effective amount of an ester according to claim 1 in admixture with a diluent.

9. A method of combating insect or acarid pests which comprises applying to the pests or a habitat thereof an insecticidally or acaricidally effective amount of O-methyl-O-[6-methylthio-pyridazin-3-yl]-ethanethionophosphonic acid ester,
O-iso-propyl-O-[6-methylthiopyridazin-3-yl]-methanethionophosphonic acid ester,
O-ethyl-O-[6-methylthiopyridazin-3-yl]-ethanethionophosphonic acid ester,
O-methyl-O-[6-ethylthio-pyridazin-3-yl]-ethanethionophosphonic acid ester, or
O-ethyl-O-[6-phenylthio-pyridazin-3-yl]-ethanethionophosphonic acid ester.